Figure 1:
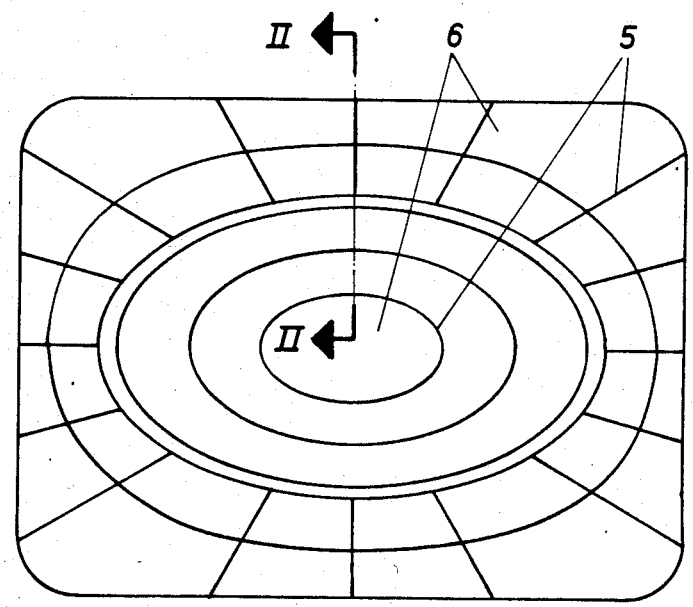

United States Patent [19]

Samuelsen

[11] Patent Number: 4,699,134
[45] Date of Patent: Oct. 13, 1987

[54] PRESSURE-RELIEVING BANDAGE

[75] Inventor: Peter B. Samuelsen, Rungsted, Denmark

[73] Assignee: Coloplast A/S, Kokkedal, Denmark

[21] Appl. No.: 692,207

[22] Filed: Jan. 17, 1985

[30] Foreign Application Priority Data

Jan. 23, 1984 [DK] Denmark .............................. 289/84

[51] Int. Cl.⁴ ............................................. A61L 15/00
[52] U.S. Cl. .................................................. 128/156
[58] Field of Search ................................ 128/156, 155

[56] References Cited

U.S. PATENT DOCUMENTS

| | | | |
|---|---|---|---|
| 3,870,593 | 3/1975 | Elton | 128/156 |
| 3,901,236 | 8/1975 | Assarsson | 128/156 |
| 3,908,648 | 9/1975 | Sandrig | 128/156 |
| 3,965,906 | 6/1976 | Karami | 128/156 |
| 3,972,328 | 8/1976 | Chen | 128/156 |
| 3,978,855 | 9/1976 | McRae | 128/156 |
| 4,161,176 | 7/1979 | Harris | 128/156 |
| 4,286,592 | 9/1981 | Chandrasekaran | 128/156 |
| 4,381,611 | 5/1983 | Wishman | 128/156 |
| 4,466,431 | 8/1984 | Tharrat et al. | 128/156 |
| 4,541,426 | 9/1985 | Webster | 128/156 |

Primary Examiner—Gregory E. McNeill
Attorney, Agent, or Firm—Kenyon & Kenyon

[57] ABSTRACT

By a pressure-relieving bandage there is arranged a flexible, non-adhesive, waterproof film (2) between a foam layer (1) and a pressure-sensitive adhesive layer (3) containing a hydrocolloid.

This will ensure that the expansion of the adhesive by moisture absorption will preferably take place in a direction away from the film (2) and in towards the body. The bandage will therefore not so easily let go of its adhesion to the skin since there is no horizontal displacement of any importance.

Moreover, the foam layer is provided with cuts (5) so that large or small sections (6) can be removed from the bandage. The plaster can therefore be used as a pressure-relieving bandage.

For prophylactic use it is advantageous to insert a micro-porous tape (7) between the foam layer (1) and the film (2) and to leave out the adhesive layer (3). Instead the underside of the tape (7) and the film (2) is adhesive and protected by a removable protective cover (4).

10 Claims, 4 Drawing Figures

PRESSURE-RELIEVING BANDAGE

The invention relates to a pressure-relieving bandage comprising a pressure-sensitive adhesive layer and a layer of flexible polymeric foam.

Bandages of this kind can advantageously be used as surgical/medical covering and dressing that can be placed adhesively on a body surface. Moreover, by suitably adapting the extent of the foam layer it is possible to pressure-relieve any desired area of the skin since the foam is placed around same, thereby absorbing and distributing the compressive stresses to which the area is subjected.

Danish Pat. No. 132,520 describes a pressure-relieving bandage of this kind where a foam pad is provided with a pressure-sensitive adhesive coating on one side. This bandage serves primarily as an adhesive foam sheet which is used for covering irregularly shaped body parts which may change shape by normal body movements.

In this product the adhesive layer has been applied directly on the foam sheet. In practice this means that polymeric foam and adhesive cannot be separated by tearing off the foam areas corresponding to the desired skin area to be pressure-relieved. When in use, the product will therefore not provide any cover for the pressure-relieved skin area, which will result in inadequate protection of the area.

Furthermore, Danish Pat. No. 147,226 describes a bandage which likewise comprises a layer of flexible polymeric foam, the cells of which are half-open, said foam being secured to an adhesive layer. The adhesive layer comprises an adhesive elastomeric material whereto there has been added granules of a hydrocolloid which will swell in water. The hydrocolloid can absorb moisture from the skin and transfer this moisture to the foam layer which will absorb the moisture and distribute same in the foam layer. This bandage is solely suitable as an absorbing bandage that cannot be used as a pressure-relieving bandage since foam cannot be removed from the adhesive layer. The foam is not separable from the adhesive layer and due to its special properties cannot be torn off or shredded and, moreover, does not have the required thickness.

It is one object of the invention to remedy the drawbacks of the known bandages and at the same time provide a product providing hitherto unknown advantages with respect to treatment as well as handling, and this is achieved in one embodiment by providing a non-adhesive, waterproof film between the adhesive layer and the foam layer.

By adding such film there is first and foremost provided a possibility of using the bandage as a pressure-relieving bandage in that foam sections can be removed by tearing them off without damaging the adhesive layer. In this manner the functional properties of the bandage are fully maintained, namely partly with an intact protective foam layer, if so desired, and partly as a pressure-relieving bandage with a fitted foam layer where the area no longer covered by foam is protected by the non-adhesive, waterproof film which will prevent adhesion of the area to clothes, bed linen and the like. The desired overall applicability of the bandage is thereby ensured.

The waterproof film moreover provides a special physical strengthening of the adhesive layer since it is compounded in such a manner that a cubic expansion takes place when the adhesive layer absorbs moisture. The film will ensure that the cubic expansion takes place in a direction away from the surface of the film and not up into a possible foam layer. This is highly desirable because the greatest possible direct contact between the adhesive and the wound area is thereby obtained and with no risk whatsoever that the adhesion to the skin is eliminated.

Finally, as a barrier to moisture, the film ensures that it is possible to use all kinds of foam that can provide the desired pressure-relieving, form-stable properties, just as the foam layer can be surface-coated, coloured, impregnated, etc.

Finally, the film provides a humid microclimate bringing about good healing results.

Preferably, the foam layer in the product can be transversely cut for forming adjoining sections, for example in patterns producing both a minimum influence of the foam on the flexibility of the product and an easy removal of foam sections according to the desired bandage geometry. The product will thus provide both good body adaption on curved as well as plane skin areas and an easy shaping of the pressure-relieved area.

By securing the foam layer and film by spot welding or spot glueing, it is possible independently of choice of materials to adjust the binding to the very optimum value.

The polymeric foam can be composed of open or closed cells, must have a specific weight $>15$ kg/m$^3$, must have a modulus of elasticity between 195 and 5 N/cm$^2$, must preferably be made of: polyvinyl chloride, polyethylene, ethylene vinyl acetate polymer or polyurethane and must have a cell number of between 10 and 200 per cm, and the foam is preferably made of ethylene vinyl acetate polymer and has approx. 50 cells per cm. The foam thickness will depend on the parameters of the foam in general, but will preferably be approx. 5 mm, with a modulus of elasticity of 110 N/cm$^2$.

A particular embodiment of the bandage is obtained by providing a layer of adhesive tape between the foam layer and the film so that the adhesive tape adheres to the film, and the foam layer is welded or glued to the adhesive tape. There is obtained an advantage by this construction when the adhesive tape is extended beyond the edges of the overlying foam layer and the underlying film layer in that in use an enhanced peripheral adhesion is obtained.

For further making the bandage comfortable in use the adhesive tape is microporous thereby ensuring the best possible ventilation of the body moisture.

The adhesive layer should have self-adhesive properties and can in a generally known manner comprise an elastomer, a hydrocolloid, a glutinous agent and a plasticizer, and the layer can have a thickness between 30$\mu$ and 1.5 mm.

Finally, it is advantageous that the film have a thickness of between 20 and 200$\mu$.

Figure 2:
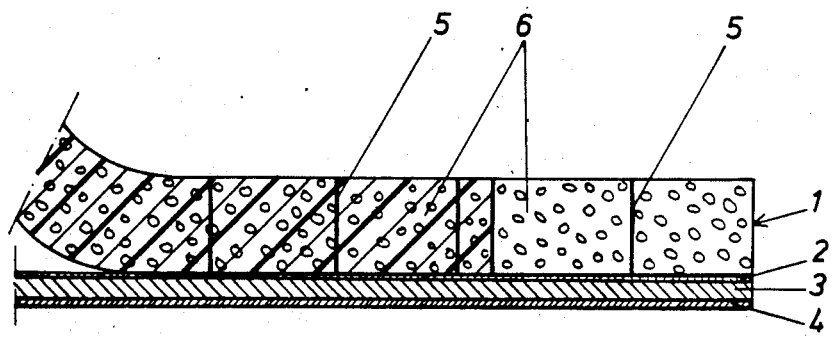
Figure 3:
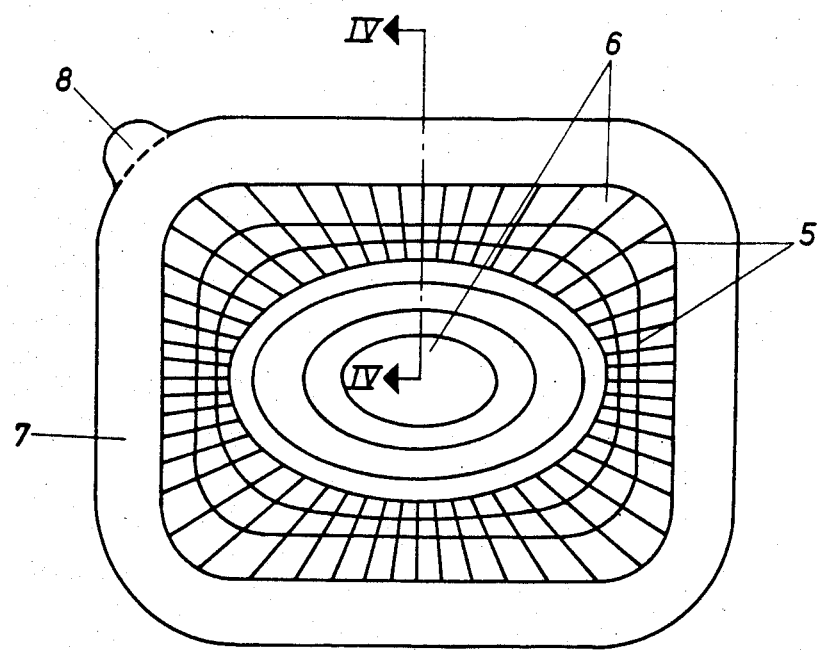
Figure 4:
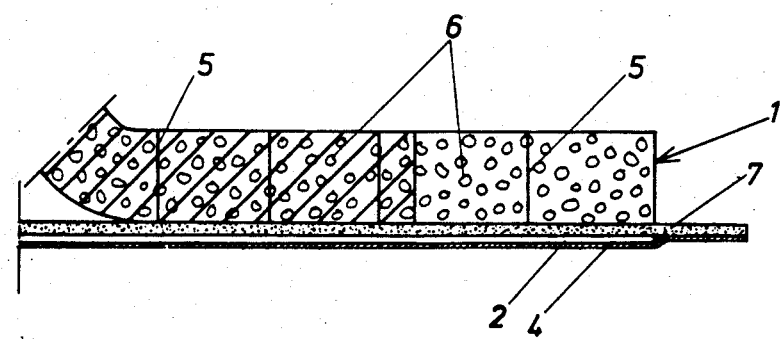

The invention will be further described in the following with reference to the drawing, wherein FIG. 1 is a bandage seen from the outside, FIG. 2 is an enlarged sectional view seen in the direction II—II in FIG. 1 and shows that a portion of the foam layer in the middle has been removed FIG. 3 is an example of an alternative embodiment of a bandage for prophylactic use, and FIG. 4 is a sectional view of the bandage seen in the direction IV—IV in FIG. 3, and where a portion of the foam layer in the middle has been removed.

FIGS. 1 and 2 schematically show an example of an embodiment of the invention.

As will appear from FIG. 2, the bandage consists of a layer of flexible foam 1 provided with a number of cuts 5 for forming separate or adjoining foam sections 6. These sections can be elliptical around the centre of the bandage, and at the outside there may be cuts extending inwardly from the edge.

This foam layer 1 is releasably secured to a flexible, waterproof film 2 extending continuously over the entire surface.

Under the film 2 there extends a pressure-sensitive adhesive layer 3 and finally there may be attached silicone paper 4 as a protective cover.

Examples of suitable foam materials are polyester or polyether polyurethane foam which can be compressed and melted together for forming a length of foam with the desired cell size, volume weight and tensile strength. A preferred amount of cells is approx. 50 cells per cm, and the finished foam layer can be approx. 5 mm thick.

A suitable film 2 is a polyurethane film which should preferably have flexible or tensile properties and which should be able to adhere to the adhesive layer by a force >100 g/2.5 cm (ASTM D 3330-76) and should by welding or adhesion be able to bind to the foam with a force >25 g/2.5 cm (ASTM D 3330-76) and should have a thickness between 20 to 200$\mu$. Such film preferably has a thickness of approx. 50$\mu$. The adhesive layer 3 is attached to the film 2.

The adhesive material 3 can be a sheet-like, gelatinous mixture of a hydrocolloid dispersed in a continuous phase consisting of a physically cross-linked elastomer such as a styrene-olefin-styrene block copolymer, a hydrocarbon gel glutinous agent, an oil extender, and an antioxidizer. Examples are self-adhesives on the basis of polyisobutylene or styrene isoprene block copolymers.

This material has good elastic and flexible properties just as it adheres well to the skin and has good storage properties. The hydrocolloid has the effect that the material can absorb secretes from the skin as well as from wounds. The adhesive will thus expand so that there is obtained good contact between the adhesive and the wound or the skin. This will provide the best conditions for quick healing, while at the same time the adhesion to the skin is reduced at these places, whereby the bandage can be removed with as little pain and inconvenience as possible to the user.

The film 2 moreover ensures that the adhesive will preferably expand in the direction away from the surface of the film layer, thereby avoiding a horizontal displacement and thus maintaining the adhesion to the skin. This is possible by the internal floating of the material.

The film 2 may be provided with a tape extension (not shown) along the outer edge of the foam section 1. The tape is adhesive on its underside, thus providing a peripheral outer adhesive area which according to requirements may provide additional adhesion to the skin, cf. the following explanation in connection with FIGS. 3 and 4.

FIGS. 3 and 4 show an example of a further embodiment of a pressure-relieving bandage which is particularly suitable for prophylactic use.

It comprises the previously mentioned foam layer 1 which is designed in conformity with the comments made on FIG. 2.

Between the foam layer 1 and the film 2 there is inserted an adhesive tape 7 which adheres to the film 2 and which is welded or glued to the foam layer 1.

As will appear from the drawing, the tape 7 extends beyond the foam layer 1 for forming a marginal zone of tape 7 for thereby obtaining a further good adhesion to the skin in use. The tape 7 is preferably microporous for giving the best possible ventilation of any body moisture.

On the adhesive underside of the tape 7 there is arranged in a generally known manner, a protective cover 4. For facilitating the removal of this cover there may be arranged a flap 8 secured to the cover so that the cover can be removed by pulling in the flap 8.

If desired, the bandage can be provided with additional properties that are wellknown to a person skilled in the art such as a frame of tape, bevellings of outer edges, use of foam laminates or another heterogeneous foam structure composition and the like.

The healing properties and the possibility of removing foam sections make the bandage ideal for healing pressure sores, and the bandage can therefore replace far more expensive and more resource demanding devices for the treatment of such sores.

I claim:

1. A bandage for providing pressure relief for portions of a skin area to be covered by the bandage, the bandage including a layer of flexible polymeric foam having an outer peripheral edge and a pressure-sensitive adhesive layer disposed on one side of the foam layer, the adhesive layer having an exposed surface facing in the same direction as said one side of the foam layer for adhering the bandage to a skin area, wherein the improvement comprises:
a non-adhesive, waterproof, flexible film arranged on the same side of the foam layer as the adhesive layer, at least part of the foam layer being secured to the film and the film extending to at least the peripheral edge of the foam layer such that the film creates a waterproof barrier on said one side of the foam layer within the area bounded by the peripheral edge of the foam layer.

2. A bandage according to claim 1 wherein the foam layer is subdivided into a plurality of adjoining sections that are selectively removable from the rest of the bandage.

3. A bandage according to claim 1 or 2 wherein the foam layer is secured to the film in localized spots.

4. A bandage according to claim 1 or 2 wherein the foam layer comprises ethylene vinyl acetate polymer and has a porosity of approximately 50 cells per cm.

5. A bandage according to claim 1 or 2 wherein the thickness of the foam layer is approximately 5 mm.

6. A bandage according to claim 1 or 2 wherein said adhesive layer comprises part of an adhesive tape disposed between the foam layer and the film, the adhesive tape having a portion extending beyond the peripheral edge of the foam layer and presenting said exposed adhesive surface facing in the same direction as the one side of the foam layer for adhering to an area of skin adjacent to a skin area bounded by the peripheral edge of the foam layer when the bandage is applied with said one side of the foam layer facing the skin area.

7. A bandage according to claim 6 wherein the adhesive tape is microporous.

8. A bandage according to claim 1 or 2 wherein the adhesive layer comprises an elastomer, a hydrocolloid, a glutinous agent, and a plasticizer and has a thickness between 30 microns and 1.5 mm.

9. A bandage according to claim 1 or 2 wherein the film has a thickness between 20 microns and 200 microns.

10. A bandage according to claim 1 or 2 wherein the adhesive layer is bonded to and is coextensive with the non-adhesive, waterproof, flexible film, said film being disposed between the foam layer and the adhesive layer.

* * * * *